United States Patent [19]
Chiang et al.

[11] Patent Number: 5,558,985
[45] Date of Patent: * Sep. 24, 1996

[54] STABLE HEMOGLOBIN REFERENCE SOLUTION

[75] Inventors: Ching Chiang, Acton; Stanley M. Liffman, Andover, both of Mass.

[73] Assignee: Bionostics Incorporated, Acton, Mass.

[ * ] Notice: The portion of the term of this patent subsequent to Mar. 27, 2009, has been disclaimed.

[21] Appl. No.: 258,505

[22] Filed: Jun. 10, 1994

Related U.S. Application Data

[63] Continuation-in-part of Ser. No. 897,316, Jun. 11, 1992, Pat. No. 5,304,491, which is a continuation-in-part of Ser. No. 328,622, Mar. 27, 1989, Pat. No. 5,045,529.

[51] Int. Cl.$^6$ .................. C12Q 1/00; C12Q 1/60; C12Q 1/56; G01N 31/00

[52] U.S. Cl. ................ 435/4; 435/11; 435/13; 435/15; 435/16; 435/18; 435/25; 436/11; 436/15

[58] Field of Search .................. 435/4, 15, 18, 435/13, 16, 25, 11; 436/11, 15

[56] References Cited

U.S. PATENT DOCUMENTS

| | | | |
|---|---|---|---|
| 3,973,913 | 8/1976 | Louderback | 23/230 |
| 4,163,734 | 8/1979 | Sorensen et al. | 252/408 |
| 4,189,401 | 2/1980 | Louderback | 252/408 |
| 4,199,471 | 4/1980 | Louderback et al. | 252/408 |
| 4,279,775 | 7/1981 | Louderback et al. | 252/408 |
| 4,289,648 | 9/1981 | Hoskins et al. | 252/408 |
| 4,299,728 | 11/1981 | Cormier et al. | 252/408 |
| 4,301,117 | 11/1981 | Smernoff | 422/99 |
| 4,401,652 | 8/1983 | Simmonds et al. | 424/101 |
| 4,469,792 | 9/1984 | Simmonds et al. | 436/11 |
| 4,485,174 | 11/1984 | Chiang et al. | 436/11 |
| 4,711,852 | 12/1987 | Jacobson | 436/15 |
| 4,753,888 | 6/1988 | Chiang | 436/11 |
| 4,843,013 | 6/1989 | Chiang | 436/11 |
| 4,945,062 | 7/1990 | Chiang | 436/11 |
| 5,013,666 | 5/1991 | Chiang | 436/11 |
| 5,045,529 | 9/1991 | Chiang et al. | 514/6 |
| 5,304,491 | 4/1994 | Chiang et al. | 436/11 |

FOREIGN PATENT DOCUMENTS

| | | |
|---|---|---|
| 0181033 | 5/1986 | European Pat. Off. . |
| 0185404 | 6/1986 | European Pat. Off. . |
| 87/06343 | 10/1987 | WIPO . |
| 90/11527 | 10/1990 | WIPO . |

OTHER PUBLICATIONS

Chanutin, A. and Curnish, R., "Effect of Organic and Inorganic Phosphates on the Oxygen Equilibrium of Human Erythrocytes", *Archives of Biochemistry and Biophysics*, 121:96–102 (1967).

Benesch, R. and Benesch, R. E., "Intracellular Organic Phosphates as Regulators of Oxygen Release by Haemoglobin", *Nature*, 221:618–622 (1969).

Masukawa, T. and Iwata, H., "Catalytic Action of Selenium in the Reduction of Methemoglobin by Glutathione", *Life Sciences*, 21:695–700 (1977).

(List continued on next page.)

*Primary Examiner*—John Kight
*Assistant Examiner*—Louise N. Leary
*Attorney, Agent, or Firm*—Hamilton, Brook, Smith & Reynolds, P.C.

[57] ABSTRACT

A reference solution for calibrating and monitoring blood gas instrumentation that has a shelf line of two years or greater is disclosed. The solution is contained in a closed container having a gas or gas mixture that is inert to the reference solution and comprises an aqueous mixture containing a hemoglobin, a source of bicarbonate ions and an organic buffer. The solution optionally contains a methemoglobin reducing system, reference concentrations of selected electrolytes, a polyphosphate compound and antibiotics. The ampule is subsequently opened and the solution is equilibrated with a gas mixture having components which provide gasses in a physiological range to the solution. The solution is characterized by exhibiting properties similar to fresh blood subsequent to equilibration.

16 Claims, 2 Drawing Sheets

OTHER PUBLICATIONS

Mansouri, A., "Hemoglobin Autoxidation Under High Oxygen Pressure Effect of Inositol Hexaphosphate", *Hemoglobin*, 5(6):579–589 (1981).

Feola, M. et al., "Development of a Bovine Stroma–Free Hemoglobin Solution as a Blood Substitute", *Surgery, Gynecology & Obstetrics*, 157(5):399–408 (Nov. 1983).

Sprokholt, R., et al. "Quality Control Material Containing Hemoglobin for Blood Gas and pH Measurement: Preparation of Stroma–free Hemoglobin Solution", *Scand J. Clin. Lab. Invest.*, 47 (188):69–82 (1987).

Matteucci, M. D. and Caruthers, M. H., "Synthesis of Deoxyoligonucleotides on a Polymer Support", *J. Am. Chem. Soc.*, 103 (31):3185–3191 (1981).

International Search Report dated 28 Jun. 1990 PCT application PCT/US90/01422.

Sprokholt, R. and Maas, A. H. J., "Evaluation of Ampouled pH and Blood Gas Quality Control Material (Prime) Based on a Stroma–Free Hemoglobin Solution (SFHS), "IFCC Workshop OSLO (1983).

STABLE HEMOGLOBIN REFERENCE SOLUTION

RELATED APPLICATION

This application is a continuation-in-part of Ser. No. 07/897,316, now U.S. Pat. No. 5,304,491, issued Apr. 19, 1994, which is, in turn, a continuation-in-part of PCT application US90/01422 filed Mar. 16, 1990, now Ser. No. 07/768,661, and which is, in turn, a continuation-in-part of Ser. No. 07/328,622 filed Mar. 27, 1989, now U.S. Pat. No. 5,045,529 issued Sep. 3, 1991.

BACKGROUND OF THE INVENTION

In practice, the use of analytical equipment for measuring various parameters of blood requires utilization of control solutions which exhibit properties as close as possible to those observed in fresh normal human blood. By measuring known parameters of control solutions, the instrumentation can be monitored and calibrated to allow highly accurate measurements of patient blood samples.

One approach to monitoring the reliability and accuracy of instruments that measure partial pressures of $CO_2$ and $O_2$ in blood is with the use of samples of fresh human blood which has been tonometered with gas mixtures having known amounts of $CO_2$, $O_2$ and $N_2$. Such a process is described by Burnett in *Clinical Chemistry*, 27(10):1761 (1981).

When the blood has been properly tonometered, the sample will have precise and fixed partial pressures of $CO_2$ and $O_2$. These prepared samples can then be introduced into the analytical instrument and $pCO_2$ and $pO_2$ values determined. Since the sample is similar to a patient blood specimen, but with known $pCO_2$ and $pO_2$ values, the instrument can be considered reliable for measuring unknown patient samples if the test values of the tonometered blood equal the theoretical values based on the gas mixture used for tonometry.

Although the use of tonometered blood is considered to be satisfactory for monitoring blood gas instrumentation, the approach has a number of drawbacks which limit its use in all but a very small percentage of laboratories.

For example, blood samples derived from human sources are susceptible to infectious agents, including hepatitis virus and HIV which can pose serious health hazards to laboratory personnel who must perform the tonometry and testing of the sample. In addition, the instruments commonly used to measure $pCO_2$ and $pO_2$ also measure blood pH. Since the tonometered blood does not have a known pH value, the sample cannot be used for monitoring the pH measurements and a separate pH control standard must be used.

Similarly, many laboratories that perform measurements of $pCO_2$, $pO_2$ and pH on blood samples also measure total hemoglobin and hemoglobin fractions on a CO-Oximeter that is located near the blood gas instrument. However, since the blood used for tonometry is acquired from random patient samples, the tonometered sample has no known hemoglobin value, and therefore it is not useful for monitoring the CO-Oximeter. Consequently, a separate control standard is required for this instrument also.

Additionally, laboratories that perform measurements of $pCO_2$, $pO_2$, pH, total hemoglobin and hemoglobin fractions, or a subset of these measurements, also often measure the amounts of various electrolytes or inorganic ions in blood samples. However, the blood used for tonometry or pH also does not have known electrolyte concentration values since the acquisition of these samples is from random individuals. Also, control standards for the monitoring of CO-oximeters do not contain specified amounts of the inorganic ions found in blood samples. Therefore, again, a separate control standard is required to monitor or calibrate instruments that measure the concentrations of these inorganic ions.

Finally, the entire procedure for properly preparing tonometered blood samples requires disciplined techniques and many laboratories lack trained personnel as well as the time to prepare the samples.

Because of these disadvantages, most laboratories use control standards which mimic human blood but have properties quite different than fresh blood. For example, buffered aqueous solutions which have been tonometered with $CO_2$ and $O_2$ are often used. These materials are assayed for predetermined values for pH, $pCO_2$ and $pO_2$. However, in composition, physical properties and chemical properties, they differ greatly from whole blood.

Other control standards comprise buffered suspensions of modified human red blood cells or hemoglobin solutions prepared from lysed red blood cells. These materials have some properties which more closely approximate actual blood than do the aqueous based controls, but their $pO_2$ buffering action and inability to provide the $O_2$ saturation characteristics of fresh blood, cause these materials to perform more like aqueous solutions than tonometered fresh blood. Furthermore, since they are prepared from human blood, the health risk to technicians is not eliminated.

In summary, the commercial blood gas controls which are used instead of tonometered fresh human blood are generally considered a compromise between convenience, economy and the ideal control standard.

A need exists for a reference solution which is not susceptible to infection, which can be packaged to eliminate the sample collection and preparation steps necessary when blood samples are used and is stable in the packaged form. Further, the solution should be capable of being tonometered in the same manner as fresh human blood to provide a control standard that has $O_2$ saturation characteristics and other properties similar to fresh human blood, but unlike the blood samples, will have predetermined pH, hemoglobin values and electrolyte concentrations for monitoring the instrument performance in the measurement of these parameters as well as $pO_2$ and $pCO_2$.

Although some of the commercial blood based materials can be used as prepackaged fluids for tonometry, the inability of these materials to be manufactured and stored without the oxidation of a significant percent of the hemoglobin to methemoglobin (which does not bind with oxygen), causes the solution to lose the oxygen saturation properties of fresh blood, and therefore makes the material unsuitable as a substitute for blood as a tonometry solution.

Attempts to provide a system for reducing methemoglobin content in a blood-based material have been the subject of a variety of scientific studies. For example, in U.S. Pat. 4,485,174 to Chiang et al., a "methemoglobin reductase" enzyme system is described as a means for maintaining a low methemoglobin level. This system, however, has demonstrated only limited usefulness, since the supply of methemoglobin reducing reagents can be exhausted when the hemoglobin solution is stored under an oxygen containing atmosphere.

Other blood-gas control solutions and methods have been described in U.S. Pat. Nos. 3,859,049; 3,973,913; 4,001,142; and 4,469,792. Additionally, a blood-gas control solution and method has been described by Steiner et al., *Clinical Chemistry*, 24, 793 (1978). Each of these, however, described a control standard having a limited storage life and/or a chemical formulation which provides physiologically inaccurate values.

Thus, a need still exists for a blood-based reference solution which, after equilibration with an appropriate gas mixture, can be used to monitor blood-gas analysis equipment. The reference solution should preferably have an extended storage life, provide physiologically accurate blood-gas values, and provide uniform values among a large number of samples.

SUMMARY OF THE INVENTION

The present invention is based on the discovery that aqueous hemoglobin reference solutions are stable for indefinite periods of time when maintained under a gas or gas mixture (preferably nitrogen with about 7% $CO_2$) that is inert towards the reference solution. Specifically, the present invention refers to a stable aqueous reference solution contained in a sealed container having a head space containing a gas or gas mixture which is inert to the reference solution. The reference solution is comprised of hemoglobin, a source of bicarbonate and an organic buffer. The container can be opened and the reference solution equilibrated by a method known as tonometry with a variety of gasses generally present in blood to provide a solution having a variety of properties similar to those properties normally found in fresh whole blood. Such an equilibrated solution has utility as a control in blood-gas analysis, CO-Oximetry instrumentation and electrolyte analysis.

Other components commonly used in reference solutions for blood-gas analysis may be added to the stable aqueous reference solution of the present invention. One such component includes the chloride ion, which, when added at suitable levels, imparts to reference solutions oxygen saturation characteristics similar to those of normal blood. The reference solution may also contain electrolytes commonly found in blood (e.g. $Na^+$, $K^+$, $Ca^{++}$, $Cl^-$), a methemoglobin reducing system, polyphosphate compound, antibacterial agents, antifungal agents and red blood cell lysing agents.

The solution is maintained in a sealed environment under a gas or gas mixture that is inert to the reference solution until shortly before use. When its use as a control is desired, the solution can be equilibrated with physiological gasses via a method such as tonometry. Once equilibrated, the system provides values of pH, $pCO_2$ and $pO_2$ suitable for monitoring Blood Gas/pH analysis instrumentation. The solution also provides physiological levels of hemoglobin and fractions of hemoglobin species for calibrating and monitoring CO-Oximetry instrumentation. The solution can also be used as a reference solution for electrolytes ($Na^+$, $K^+$, $Ca^{++}$, $Cl^-$).

Finally, the solution also exhibits oxygen saturation characteristics similar to those of fresh whole blood. Prior to equilibration with physiological gases ($O_2$ and $CO_2$), the solution can serve as the lower limit for a linearity standard for $pO_2$ and oxyhemoglobin. This solution can also serve as a control for measuring $pCO_2$ or pH. Tonometry of the solution with predetermined amounts of oxygen can provide solutions with specified $pO_2$ values of the linearity standard and saturation of the solution with oxygen can provide the upper limit of the linearity standard.

DETAILED DESCRIPTION OF THE INVENTION

The present invention is a stable reference solution for, inter alia, blood gas, CO-Oximetry and electrolyte instrumentation. Unlike solutions previously employed for calibration and monitoring of blood gas/CO-Oximetry equipment in which physiological gasses are present in solution during storage, the present solution comprises a stable, aqueous, hemoglobin solution which is equilibrated with physiological gasses just prior to use. This solution, and equilibration method associated therewith, provide a blood gas reference solution having a storage life which is longer than that of previously employed controls. This is achieved in part through the use of a metal ion catalyzed methemoglobin reducing system which serves to inhibit formation of undesirable methemoglobin during storage, gas equilibration and use.

A cell-free hemoglobin solution is prepared from healthy animal blood. In the preferred embodiment, the hemoglobin source is bovine, rather than human, blood. Although modified human red blood cell solutions, as well as stroma-free human hemoglobin solutions, are commercially available, these human-source solutions are susceptible to contamination by a variety of human infectious agents including the hepatitis virus and HIV. The use of non-human blood products in blood-based reference solutions is therefore desirable. As such, the use of bovine blood collected from healthy animals is preferred due to its similarity to human blood in both physical and chemical characteristics.

Additionally, the present invention exhibits oxygen saturation characteristics which are more similar to those of fresh whole blood than have been seen in other control standards. For example, when oxygen saturation is plotted against partial pressure, known reference solutions exhibit a hyperbolic curve. In contrast, the present solution, like fresh whole blood, exhibits a sigmoid curve. Furthermore, values for the required oxygen partial pressure to achieve 50% saturation, the so-called $P_{50}$ value, have been established for a set of reference solutions of this invention by varying the chloride ion concentrations of these solutions. Table I summarizes the effects of different chloride ion concentrations on the $P_{50}$ values of solutions of this invention.

TABLE I

| [$Cl^-$] | $P_{50}$ |
|---|---|
| below 60 mM | <24 mm Hg |
| 70–90 mM | 26 mm Hg |
| 95–105 mM | 28 mm Hg |
| 115–125 mM | 30 mm Hg |

The $P_{50}$ values, obtained for tonometered hemoglobin $P_{50}$ solutions made from bovine erythrocyte derivatives, were in the range of 24 to 32 mmHg. These values are well within the normal $P_{50}$ range for fresh human blood of 20 to 34 mm Hg.

Figure 1:
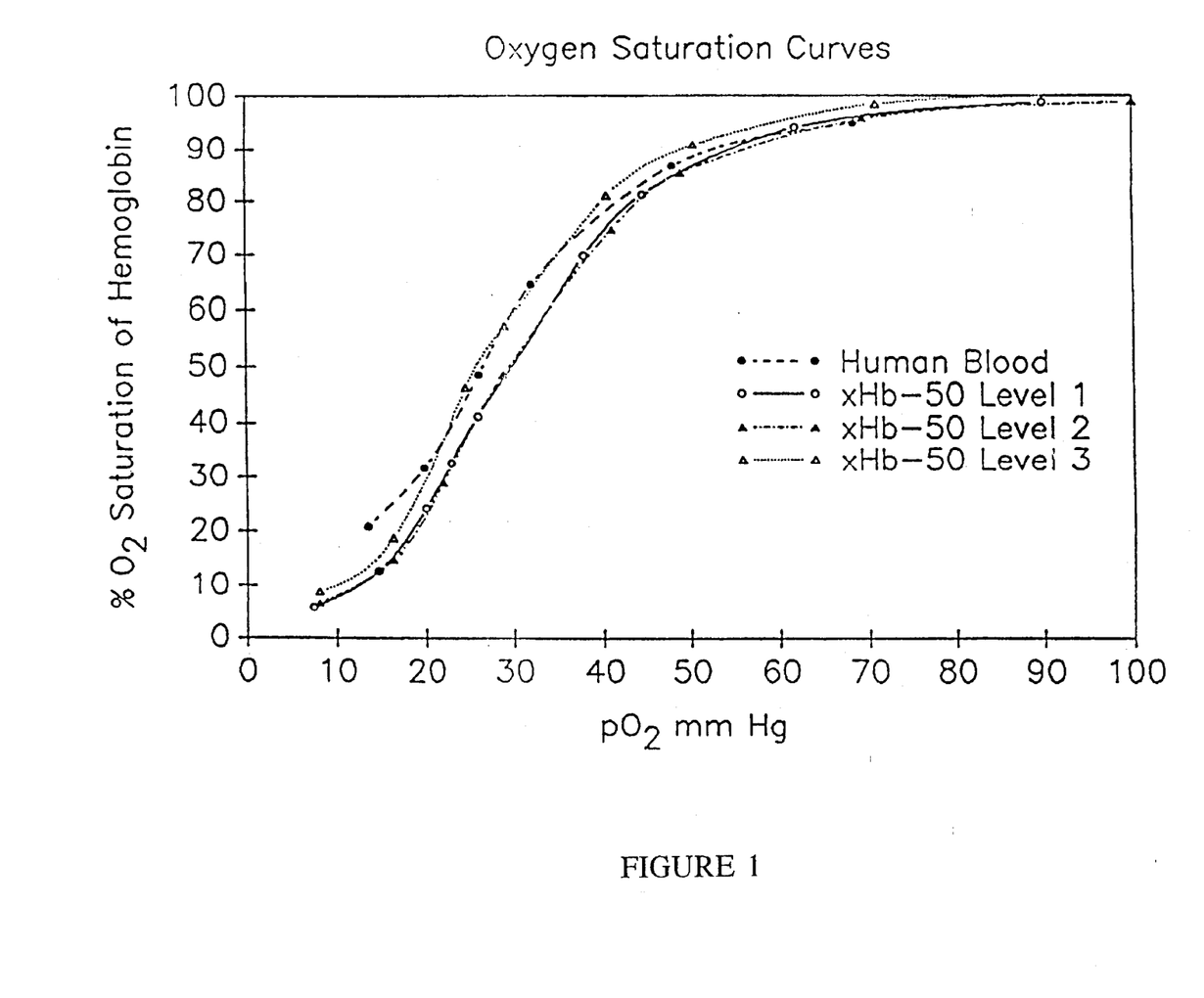
FIG. 1 shows oxygen saturation curves (% $O_2$ saturation of hemoglobin as a function of pO2) for three levels of the reference solution and for fresh human blood.

The Figure shows the oxygen saturation curves for three tonometered hemoglobin $P_{50}$ reference solutions prepared with chloride ion concentrations of 116 mM, 97 mM and 82 mM for Level I, Level II and Level III, respectively. The three reference solutions were equilibrated with at least seven different concentrations of oxygen gas containing a constant concentration of $CO_2$. These oxygen saturation curves are remarkably similar to that for fresh human blood. The $P_{50}$ values of these reference solutions bracket the $P_{50}$ value of fresh human blood as shown in the Figure.

As a source of hemoglobin in the present invention, red blood cells are collected by centrifugation of the animal blood and washed repeatedly with 0.9% saline. Subsequently, the washed red blood cells are lysed by the addition of three volumes of 5mM phosphate buffer, pH 7.2, which results in completely lysed ghost cells, stroma fragments and hemoglobin in solution. The ghost cells and stroma fragments are then removed by passing the hemoglobin-containing filtrate through a 0.22 µm cross-flow microfiltration unit. At this point, antibiotics, such as gentamycin sulfate, streptomycin, or penicillin G can be added to minimize microbial contamination in the further preparation steps. The concentration of hemoglobin is usually at 6 to 7 gm % and can be further concentrated to various levels by subjecting the hemoglobin solution to a filtration procedure with an ultra-filtration unit which has a cutoff limit of 10,000 molecular weight.

The methemoglobin reducing system, when desired, is now added to the completely lysed hemoglobin solution. A methemoglobin reducing system is not essential, particularly for hemoglobin $P_{50}$ reference solutions. For such reference solutions, when a methemoglobin reducing system is desired, any such system can be employed including systems using methemoglobin reductase. For most of the reference solutions of the present invention, a methemoglobin reducing system is preferred. The preferred methemoglobin reducing system in the present invention comprises a sulfhydro compound selected from the class of chemicals which have an effective thio (-SH) functional group. Such chemicals include, but are not limited to the reduced form of glutathione, mercaptoethanol, cysteine and their derivatives. A catalytic amount of a metal ion is provided to the solution via salts of selenium, tellurium, and copper which are added to the solution to catalyze the methemoglobin reduction reaction. Such a metal ion catalyzed methemoglobin reducing system is described by Masukawa and Iwata in *Life Sciences*, 21(5), 695 (1977), the teachings of which are incorporated herein by reference. In this reference, selenite, selenate, and selenocystine are described as catalysts for reactions in which methemoglobin is reduced by glutathione, 2-mercaptoethylamine and cysteine.

Additionally, further resistance to methemoglobin formation can be imparted to the solution by the addition of a polyphosphate compound. This compound stabilizes the hemoglobin molecules in a spatial configuration which is not readily oxidized to the methemoglobin form. Preferred polyphosphate compounds include 2,3-diphosphoglycerate, inositol hexaphosphate (also referred to as phytic acid), and adenosine triphosphate. The use of a polyphosphate to stabilize hemoglobin was described in greater detail by Mansouri in *Hemoglobin*, 5(6), 579 (1981), the teachings of which are incorporated herein by reference.

Following the addition of the hemoglobin stabilizing systems described above, if such hemoglobin stabilizing systems are desired, the pH of the solution is adjusted to within a physiological range. In the preferred embodiment, the pH is adjusted to between about 7.0 and 7.6 using aqueous NaOH under an inert atmosphere such as nitrogen or noble gas. A source of bicarbonate ion, preferably sodium bicarbonate and a suitable organic buffer selected from Good's buffers and their derivatives are added to buffer the ph. Preferable buffers include N-2-hydroxyethylpiperazine-N'-2-ethane sulfonic acid (HEPES; $pK_a = 7.31$), 3-[N-bis(hydroxyethyl)-amino]-2-hydroxypropane sulfonic acid (DIPSO; $pK_a = 7.35$), piperazine-N-N'-Bis (2-hydroxypropane sulfonic acid) (POPSO; $pK_a = 7.63$), 3-[N-(Trishydroxymethyl) methylamino]-2-hydroxypropane sulfonic acid (TAPSO; $pK_a = 7.39$), and N-hydroxyethyl-piperazine-N'-2-hydroxypropane sulfonic acid (HEPPSO; $pK_a = 7.73$).

Various amounts of salt solutions of sodium, potassium, calcium and chloride are added to adjust the concentrations of these ions to achieve the desired levels. The amount of sodium which is added is adjusted to account for the sodium which was previously added as sodium bicarbonate. The resultant solution is then passed through a 0.2 µm sterile filter to remove any microbial contamination that may be present. Optionally, an antifoaming agent can be added before filtration.

The hemoglobin solution is then further bubbled with nitrogen or other inert gasses which contain between about 2 to about 12% carbon dioxide. This nitrogen bubbling step serves to convert any oxyhemoglobin in solution to reduced hemoglobin and to maintain anaerobic conditions. The carbon dioxide in the gas mixture is used to maintain an acceptable pH value between about 7.0 and 7.2 in the solution. The solution is then sealed in a container, such as glass ampule, under an atmosphere like that bubbled through the solution.

The resulting hemoglobin contained in the aqueous solution preferably comprises hemoglobin fractions of at least about 95% reduced hemoglobin, less than 3% methemoglobin, less than 3% oxyhemoglobin, less than 2% carboxyhemoglobin and less than 0.3% by volume oxygen. The solution has a purple-blue color as a result of the reduced hemoglobin contained therein. As there are few, if any, oxidizing agents (including molecular oxygen) in solution, the formation of methemoglobin is almost completely eliminated. As there is only negligible methemoglobin in solution, the methemoglobin reducing system is not utilized at this point. Rather, the system will serve to prevent methemoglobin production during a subsequent gas equilibration just prior to solution use.

When the solution is to be used for monitoring of blood gas/CO-Oximetry instruments, it must first be equilibrated with a physiological gas mixture. In the preferred method, this equilibration is performed via tonometry. Tonometry is the term used to describe the process whereby a liquid is brought into equilibrium with a gas phase by either bubbling the desired gas through the liquid or by forming a liquid film with large surface area interacting with the incoming gas. A detailed discussion of tonometry is provided by R. W. Burnett in *Clincal Chemistry*, 27(10), 1761 (1981), the teachings of which are incorporated herein by reference. During the tonometry (or even when exposed to ambient air) the solution rapidly changes from the purple-blue color indicative of the presence of reduced hemoglobin to a red color indicative of the presence of oxyhemoglobin. The amount of methemoglobin produced during the tonometry remains minimal due to the metal ion catalyzed methemoglobin reduction system described previously.

Upon completion of the equilibration, the solution will contain known, predetermined levels of pH, $pCO_2$ and $pO_2$. Thus the solution can be analyzed by a Blood Gas/pH Analyzer and can be used to monitor the instrumentation and ensure a minimum drift from the set-point. The solution can also be used for the calibration and monitoring of CO-Oximetry equipment used to measure levels of total hemoglobin and fractions of hemoglobin species. The same equilibrated solution can also be used for the monitoring of electrolyte analyzers which detect and quantify the ions of sodium, potassium, calcium and chloride.

In addition, the reference solution can be used as a linearity control solution for monitoring $pO_2$, oxyhemoglobin and deoxyhemoglobin. The linearity of the $pO_2$, as measured in a blood gas analyzer, or the % oxyhemoglobin and % deoxyhemoglobin fractions, as measured in a CO-Oximeter, can be tested by using a fresh ampule of the reference hemoglobin solution. The linearity test can be initiated by simply opening the ampule and analyzing it immediately in the blood gas analyzer or the CO-Oximeter. The $pO_2$ and % oxyhemoglobin will be very low and the % deoxyhemoglobin will be very high. Equilibrating the opened reference hemoglobin solution with room air by shaking it vigorously for 5–10 minutes will yield a hemoglobin solution with close to 100% oxygen saturation, when measured in a blood gas analyzer, as well as close to 100% oxyhemoglobin and 0% deoxyhemoglobin, when measured in a CO-Oximeter. Thus, the extreme linearity limits of $pO_2$, % oxyhemoglobin and % deoxyhemoglobin can be easily checked with the reference solution of the present invention.

In a preferred embodiment, the solution is representative of normal human blood. In this embodiment, the solution has the following composition:

| Component | Range | Specific |
|---|---|---|
| Total Hemoglobin | 13–15 g/dl | 14 g/dl |
| Sodium Selenite | 1–20 µM | 4.2 µM |
| Phytic Acid | 0.1–1.4 mM | 0.2 mM |
| Reduced Glutathione | 0.5–8 mM | 3.0 mM |
| HEPES | 20–50 mM | 40 mM |
| Sodium (ionized) | 135–145 mM | 140 mM |
| Potassium (ionized) | 4–6 mM | 5 mM |
| Calcium (ionized) | 1.0–1.3 mM | 1.2 mM |
| Chloride (ionized) | 95–105 mM | 100 mM |
| Sodium bicarbonate | 24–27.2 mM | 25.6 mM |
| Gentamycin sulfate | 20–40 ppm | 30 ppm |
| Streptomycin | 40–60 ppm | 50 ppm |
| Penicillin G | 40000–60000 units | 50000 units |

Upon use, this solution is equilibrated via tonometry with a gas mixture which comprises by volume 5.6% $CO_2$, 9.8% $O_2$ and 84.6% $N_2$. This equilibration is carried out at 37° C. until the pH is within the range of about 7.38 to about 7.42, the $pCO_2$ is within the range of about 38 to about 42 mmHg, and the $pO_2$ is within the range of about 67 to about 73 mmHg when the tonometry is carried out at the standard barometric pressure of 760 mm Hg. In a most preferred embodiment, following equilibration, the solution will have a pH of about 7.40, a $pCO_2$ of about 40 mmHg and a $pO_2$ of about 70 mmHg at 37° C.

In another preferred embodiment, the solution is representative of the blood of a human patient experiencing acidosis. In this embodiment, the solution has the following composition:

| Component | Range | Specific |
|---|---|---|
| Total Hemoglobin | 17–19 g/dl | 18 g/dl |
| Sodium Selenite | 1–20 µM | 4.2 µM |
| Phytic Acid | 0.1–1.4 mM | 0.2 mM |
| Reduced Glutathione | 0.5–8 mM | 3.0 mM |
| HEPES | 20–50 mM | 40 mM |
| Sodium (ionized) | 150–160 mM | 155 mM |
| Potassium (ionized) | 6–8 mM | 7 mM |
| Calcium (ionized) | 1.4–1.8 mM | 1.6 mM |
| Chloride (ionized) | 115–125 mM | 120 mM |
| Sodium bicarbonate | 25.2–28.4 mM | 26.8 mM |
| Gentamycin sulfate | 20–40 ppm | 30 ppm |
| Streptomycin | 40–60 ppm | 50 ppm |
| Penicillin G | 40000–60000 units | 50000 units |

Upon use, this solution is equilibrated via tonometry with a gas mixture which comprises by volume 9.8% $CO_2$, 14.0% $O_2$ and 76.2% $N_2$. This equilibration is carried out at 37° C. until the pH is within the range of about 7.18 to about 7.22, the $pCO_2$ is within the range of about 67 to about 73 mmHg, and the $pO_2$ is within the range of about 97 to about 103 mmHg. In a most preferred embodiment, following equilibration, the solution will have a pH of about 7.20, a $pCO_2$ of about 70 mmHg and a $pO_2$ of about 100 mmHg at 37° C.

In yet another preferred embodiment, the solution is representative of the blood of a human patient experiencing alkalosis. In this embodiment, the solution has the following composition:

| Component | Range | Specific |
|---|---|---|
| Total Hemoglobin | 8–10 g/dl | 9 g/dl |
| Sodium Selenite | 1–20 µM | 4.2 µM |
| Phytic Acid | 0.1–1.4 mM | 0.2 mM |
| Reduced Glutathione | 0.5–8 mM | 3.0 mM |
| HEPES | 20–50 mM | 40 mM |
| Sodium (ionized) | 115–125 mM | 120 mM |
| Potassium (ionized) | 2–4 mM | 3 mM |
| Calcium (ionized) | 0.6–0.8 mM | 0.7 mM |
| Chloride (ionized) | 70–90 mM | 80 mM |
| Sodium bicarbonate | 17.4–20.6 mM | 19.0 mM |
| Gentamycin sulfate | 20–40 ppm | 30 ppm |
| Streptomycin | 40–60 ppm | 50 ppm |
| Penicillin G | 40000–60000 units | 50000 units |

Upon use, this solution is equilibrated via tonometry with a gas mixture which comprises by volume 2.8 $CO_2$, 5.6% $O_2$ and 91.6% $N_2$. This equilibration is carried out at 37° C. until the pH is within the range of about 7.57 to about 7.63, the $pCO_2$ is within the range of about 18 to about 22 mmHg, and the $pO_2$ is within the range of about 37 to about 43 mmHg. In a most preferred embodiment, the solution will have a pH of about 7.60, a $pCO_2$ of about 20 mmHg and a $pO_2$ of about 40 mmHg at 37° C.

Another embodiment of the present invention is based on the discovery that aqueous hemoglobin reference solutions are stable up to two years and longer when stored at appropriate temperatures under gas or gas mixtures that are inert to the reference solution. Stable as defined herein, refers to reference solutions wherein the methemoglobin and reduced hemoglobin level remain constant. Specifically, the present invention relates to a stable aqueous reference solution for blood gas, CO-Oximetry and electrolyte instrumentation contained in a sealed container. In the head space above the reference solution is contained a gas or gas mixture which is inert to the reference solution. The stable aqueous reference solution is comprised of hemoglobin, a source of bicarbonate ions and an organic buffer. Appropriate temperatures for storage are from 0° C. to room temperature, with 4° C. being preferred. The stable reference solution of the present embodiment can be conveniently stored until immediately prior to use, when the container is opened and the solution removed for its designated use.

The hemoglobin of the present embodiment is prepared from human blood or bovine blood, as described hereinabove. Bovine blood is preferred to eliminate the risk of hepatitis or HIV infection. The hemoglobin solution may contain stroma fragments but stroma free solutions are preferred. The pH of the reference solution is adjusted to within a physiological range. In a preferred embodiment, the pH is adjusted to between about 7.0 to 7.6 using aqueous NaOH under an inert atmosphere such as nitrogen or noble gas. A source of bicarbonate ion, preferably sodium bicarbonate, and a suitable buffer are added to buffer the pH. Suitable organic buffers are selected from Good's buffers and their derivatives, as described hereinabove.

The inert gases in the head space above the stable reference solution can include nitrogen, noble gases, and mixtures thereof. Nitrogen is preferred. In addition, the gas or gas mixture may contain up to 12% $CO_2$. As discussed hereinabove, the same or similar inert gas or gas mixture is bubbled through the reference solution prior to its being sealed in a container such as an ampule. Bubbling an inert gas or gas mixture through the reference solution serves to remove oxygen dissolved in the aqueous reference solution and convert oxyhemoglobin to reduced hemoglobin. Sealing the aqueous reference solution in a container under a head of a gas or gas mixture which is inert to the reference solution maintains the reduced hemoglobin at a desired level by preventing oxygen from dissolving in the reference solution and oxidizing reduced hemoglobin to methemoglobin. This maintenance of reduced hemoglobin levels extends shelf life of the reference solutions of the present invention. Preferably, the fraction of reduced hemoglobin in the aqueous reference solution is maximized, i.e., the bubbling of the inert gas or gas mixtures through the reference solution is continued until the reference solution comprises hemoglobin fractions of at least 95% reduced hemoglobin, less than 3% methemoglobin, less than 3% oxyhemoglobin, less than 2% carboxyhemoglobin and less than 0.3% by volume oxygen. Because blood-gas control solutions can have lower fractions of reduced hemoglobin, the present invention also contemplates aqueous reference solutions with lower reduced hemoglobin levels, for example from about 60% to about 95%. In another aspect of this invention, small amounts of oxygen remain dissolved in the aqueous reference solution or in the head space above the aqueous reference solution in the sealed container. Oxygen remaining within the sealed container oxidizes reduced hemoglobin, thereby reducing its level within the aqueous reference solution. Acceptable amounts of oxygen which can remain within the sealed container are those which do not cause the level of reduced hemoglobin to fall below fractions suitable for use in blood-gas control solutions. Normally, $pO_2$ levels of less than 5 mm Hg are acceptable.

Other components normally present in blood-gas control solutions, may be added to the stable aqueous reference solution prior to its being sealed in a container under a gas or gas mixture which is inert to the reference solution. Suitable components have been described hereinabove for other reference solutions of the present invention, and impart desirable properties to the stable aqueous reference solution. For example, chloride ion concentrations affect the $P_{50}$ value of the reference solution, as summarized in Table 1. The chloride ion concentration can be changed in the aqueous reference solution to vary the $P_{50}$ value of the solution. Preferably, the aqueous reference solution has a chloride ion concentration such that the $P_{50}$ value is within the range of human blood, i.e. from 20 mm to 34 mm Hg.

The stable aqueous reference solution may optionally comprise a methemoglobin reducing system. One such suitable system, which is comprised of a thio functional group provided by 1) a sulfhydro compound selected from the group consisting of reduced glutathione, mercaptoethanol, cysteine and derivatives thereof, and 2) a source of metal ion catalysts provided by a salt of metals selected from the group consisting of selenium, tellurium and copper, has been described hereinabove. Another suitable reducing system is an enzyme system described in U.S. Pat. No. 4,485,174 to Chiang et al., the contents of which are expressly incorporated herein by reference. This reducing system is comprised of a reduced pyridine nucleotide capable of participating in a reaction which reduces methemoglobin to normal hemoglobin, L-lactic acid, lactate dehydrogenase and hemoglobin reductase. Preferred pyridine nucleotides are NADH and NADPH.

Another optional component which may be added to the stable aqueous reference solution prior to its being sealed in a container under a head of a gas or gas mixture which is inert to the reference solution includes a polyphosphate compound to impart further resistance to methemoglobin formation. Salt or salt solutions which contain electrolytes present in normal blood may also be added. Salt solutions of sodium, potassium, calcium and chloride are suitable examples. Additional components which may be added to the stable reference solution prior to sealing under an inert gas include antibacterial agents (e.g. gentamycin sulfate, streptomycin and penicillin), antifungal agents and red blood cell lysing agents. The use of polyphosphate compounds, salt solutions, antibacterial agents, antifungal agents and blood cell lysing agents in blood-gas control solutions are described in greater detail hereinabove.

In a preferred embodiment, the additional components are added to the aqueous reference solution in proper concentrations such that the reference solution is representative of normal human blood. In another embodiment, the additional components are added to the aqueous reference solution in proper concentrations such that the reference solution is representative of the blood of a patient with alkalosis. In yet another embodiment of the present invention, the additional components are added to the aqueous reference solution in proper concentrations such that the reference solution is representative of the blood of a patient with acidosis. The compositions and methods of equilibration of these solutions are described hereinabove.

The stable aqueous reference solutions in sealed containers stored under a head space containing a gas or gas mixture inert to the reference solution are used for monitoring blood gas/CO-Oximetry instruments. Immediately after opening, and prior to tonometry, the reference solutions can serve as a control or as a calibrator for the low linearity limits for $pO_2$ and % oxyhemoglobin as well as the high linearity limit for % deoxyhemoglobin. When used for the monitoring of blood-gas/CO-Oximetry equipment is desired, the container is opened and subjected to tonometry as previously described.

EXAMPLE 1

A Preferred Batch Protocol for Producing a Large Volume of Reference Solution Representative of Normal Blood Reagents:

(A) Bovine red blood cell suspension (B) Aqueous solution containing 0.00144% $Na_2SeO_3$ and 0.187% Phytic Acid (C) 190.6 g HEPES plus 17.65 g NaOH in one liter of deionized water to provide a pH of about 7.4.

(D) 19.67 g reduced glutathione in 1 liter of deionized water (E) 5 mM phosphate buffer, pH 7.2 (0.39 g $Na_2HPO_4$ and 0.145 g $NaH_2PO_4$ in 1 liter of deionized water)

Procedures:

1) Wash the bovine red blood cell suspension with saline solution at least four times.

2) Lyse the red blood cells by the addition of three volumes of 5 mM phosphate buffer, pH 7.2. Adjust the pH of the hemoglobin solution to 7.8 with NaOH. Add $CaCl_{12}$ and phytic acid to provide up to final concentrations of 10 mM $CaCl_2$ and 0.125 mM phytic acid (inositol hexaphosphate).

3) Pass the lysate through a 0.22 μm cross-flow microfiltration unit and collect the filtrate.

4) Antibiotics are optionally added to final concentrations of gentamycin 30 ppm, Streptomycin 50 ppm, and penicillin G 50000 units, respectively, to minimize microbial contamination. The solution can be stored at 4°–8° C. if necessary.

5) The hemoglobin solution thus prepared is concentrated to higher levels as desired by the use of a cross-flow ultra-filtration unit with a cut-off limit of 10000 molecular weight.

6) To every 800 ml of concentrated hemoglobin solution obtained in step (5) add 50 ml each of reagents (B), (C) and (D) resulting in a total volume of about 950 ml.

7) Various amounts of salt solutions made of sodium, potassium, calcium, and chloride in deionized water are added to reach the desired levels (the amount of sodium added in this step takes into account the sodium added as sodium bicarbonate in step 10) below).

8) The pH of the solution is adjusted to 7.4 by slowly adding a 4% aqueous NaOH solution under a nitrogen (100%) atmosphere.

9) Finally, deionized water is added to bring the total volume to one liter.

10) 2.15 g/L solid $NaHCO_3$ is added to the solution.

11) The hemoglobin solution is filtered through a sterile filter having a maximum pore size of about 0.2 μm.

12) A small quantity of defoamer made of mineral oil or silicone based antifoam A concentrate is added to the solution.

13) The hemoglobin solution is flushed with nitrogen gas containing about 4 to 7% $CO_2$ at 4 to 8° C., or at room temperature until the oxyhemoglobin value is less than 3% of the total hemoglobin.

14) The hemoglobin solution is sterilely filtered through a 0.2 μm filter and the solution is subdivided into individual sealed ampules having the gas mixture of step 13) contained in the head space.

EXAMPLE 2

Stability of the Reference Solutions Stored in Sealed Ampules Under a Head of Nitrogen and $CO_2$ The resulting sealed ampules from Example 1 were divided into three groups. Group One was stored at 4° C., Group Two was stored at room temperature and Group Three was stored at 37° C. At time periods ranging from 10 to 180 days, an ampule from each of the three groups was opened and equilibrated via tonometry with a gas mixture which comprises by volume 56% $CO_2$, 9.8% $O_2$ and 84.6% $N_2$. This equilibration was carried out at 37° C. by bubbling the gas mixture through the reference solution with the solution having a final pH of about 7.40, a $pCO_2$ of about 40 mm Hg and a $pO_2$ of about 70 mm Hg at 37° C. The amount of methemoglobin in each of the three equilibrated reference solutions was then determined by IL 282 CO-oximeter. The results are shown in graph form in FIG. 2.

Figure 2:
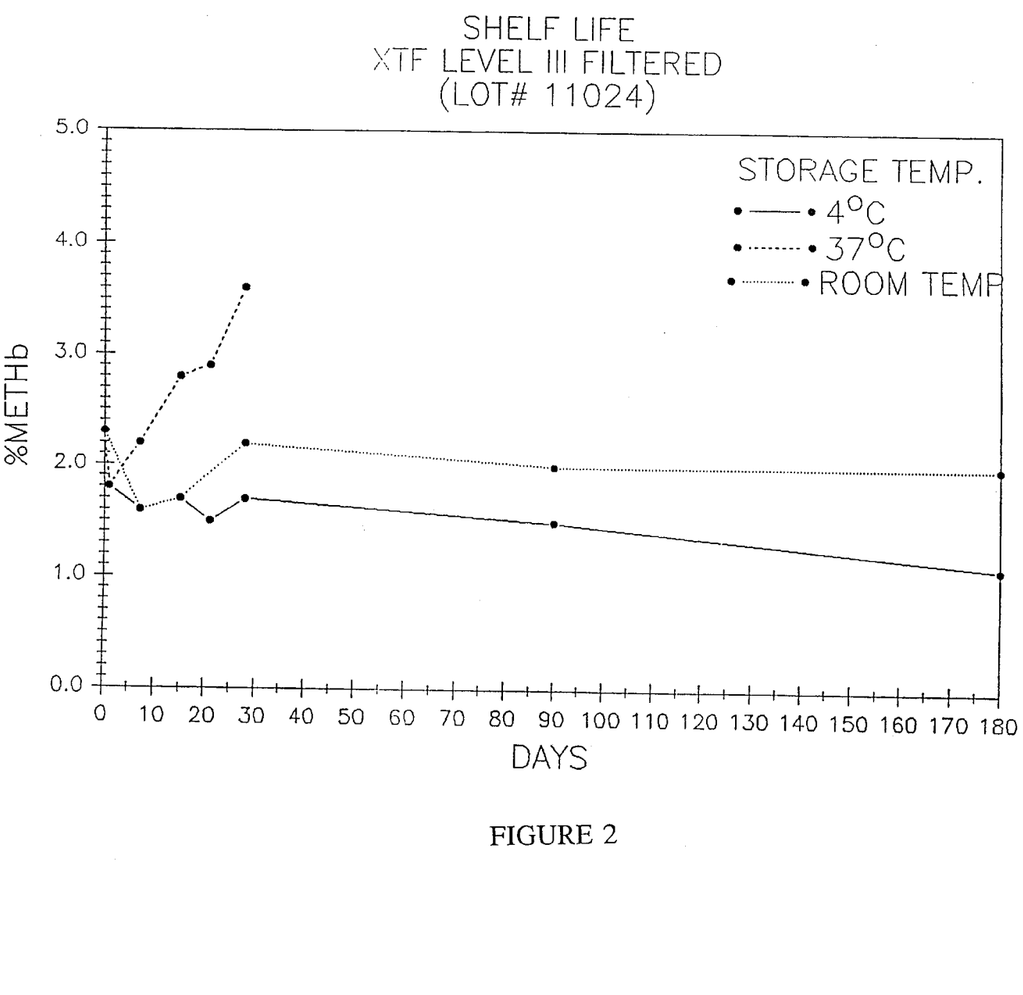
FIG. 2 shows in graphical form the percent of methemoglobin present over a period of 180 days in stable aqueous reference solutions of the present invention when stored in sealed containers under a head of nitrogen containing 7% $CO_2$ at either 4° C., room temperature or 37° C.

FIG. 2 indicates that the percentage of methemoglobin in the reference solution stored at 4° C. remains essentially unchanged at about 1.5 –2.0% over a period of 120 days. The reference solution stored at room temperature has somewhat higher levels of methemoglobin at 30 to 180 days (2.0 to 2.3%), but still exhibits relatively good stability. The reference solution stored at 37° C. shows significant deterioration after 10 days, with methemoglobin levels doubling within 30 days.

These results show that hemoglobin-containing aqueous reference solutions used to monitor blood-gas analysis equipment are stable when stored in sealed containers under head gas mixtures that are inert to the reference solution. These reference solutions are stable for 180 days and beyond when stored at room temperature and below, preferably at 4° C.

Equivalents

Those skilled in the art will recognize, or be able to ascertain using no more than routine experimentation, many equivalents to the specific embodiments of the invention described herein. Such equivalents are intended to be covered by the following claims.

We claim:

1. A stable aqueous reference solution which is contained in a sealed container having a head space consisting essentially of gas which is inert to the reference solution, wherein the stable aqueous reference solution comprises:

a) hemoglobin;

b) a source of bicarbonate ions; and c) an organic buffer.

2. A stable reference solution of claim 1, wherein the head space further comprises $CO_2$.

3. The stable reference solution of claim 2, wherein the hemoglobin is isolated from human blood.

4. The stable reference solution of claim 2, wherein the hemoglobin is isolated from bovine blood.

5. The stable reference solution of claim 2, wherein the stable reference solution is stable for at least three months.

6. A stable reference solution of claim 2, wherein the headspace contains at least about 93% inert gas selected from the group consisting of nitrogen, noble gases and mixtures thereof, and the remainder of the gas comprising $CO_2$.

7. A stable reference solution of claim 2 having a $P_{50}$ value of between about 20 mm to about 34 mm Hg.

8. A stable reference solution of claim 2, wherein the hemoglobin is stroma free.

9. A stable reference solution of claim 2, further comprising a methemoglobin reducing system.

10. The stable reference solution of claim 9, wherein the methemoglobin reducing system comprises:

a) thio functional groups provided by a sulfhydro compound selected from the group consisting of reduced glutathione, mercaptoethanol, cysteine and derivatives thereof; and b) a source of metal ion catalysts provided by a salt of metals selected from the group consisting of selenium, tellurium and copper.

11. The stable reference solution of claim 9, wherein the methemoglobin reducing system comprises of a reduced pyridine nucleotide capable of participating in a reaction which reduces methemoglobin to normal hemoglobin, L-lactic acid, lactate dehydrogenase and hemoglobin reductase.

12. The stable reference solution of claim 11, wherein the reduced pyridine nucleotide is NADH or NADPH.

13. The stable reference solution of claim 2, wherein:
a) the hemoglobin comprises between about 13 and about 15 g/dl bovine hemoglobin solution, said hemoglobin solution comprising fractions of:
   i) at least about 95% reduced hemoglobin;
   ii) less than about 3% methemoglobin;
   iii) less than about 2% carboxyhemoglobin;
   iv) less than about 3% oxyhemoglobin; and
   v) less than about 0.3% by volume oxygen;
b) the concentration of bicarbonate ions ranges from about 24 to about 27.2 mM; and
c) the organic buffer is HEPES buffer with a concentration range from about 20 to about 50 mM;
d) wherein the stable reference solution further comprises:
   i) a concentration of sodium selenite ranging from about 1.0 to about 20 µM;
   ii) a concentration of phytic acid ranging from about 0.1 to about 1.4 mM;
   iii) a concentration of reduced glutathione ranging from about 0.5 to about 8 mM;
   iv) a concentration of sodium ions ranging from about 135 to about 145 mM;
   v) a concentration of potassium ions ranging from about 4 to about 6 mM;
   vi) a concentration of calcium ions ranging from about 1.0 to about 1.3 mM;
   vii) a concentration of chloride ions ranging from about 95 to about 105 mM.

14. The stable reference solution of claim 2, wherein:
a) the hemoglobin comprises between about 17 and about 19 g/dl bovine hemoglobin solution, said hemoglobin solution comprising fractions of:
   i) at least about 95% reduced hemoglobin;
   ii) less than about 3% methemoglobin;
   iii) less than about 2% carboxyhemoglobin;
   iv) less than about 3% oxyhemoglobin;
   v) less than about 0.3% by volume oxygen;
b) the concentration of bicarbonate ions ranges from about 25.2 to about 28.4 mM; and
c) the organic buffer is HEPES buffer with a concentration range from about 20 to 50 mM;
d) wherein the stable reference solution further comprises:
   i) a concentration of sodium selenite ranging from about 1 to about 20 µM;
   ii) a concentration of phytic acid ranging from about 0.1 to about 1.4 mM;
   iii) a concentration of reduced glutathione ranging from about 0.5 to about 8 mM;
   iv) a concentration of sodium ions ranging from about 150 to about 160 mM;
   v) a concentration of potassium ions ranging from about 6 to about 8 mM;
   vi) a concentration of calcium ions ranging from about 1.4 to about 1.8 mM; vii) a concentration of chloride ions ranging from about 115 to about 125 mM.

15. The stable reference solution of claim 2, wherein:
a) the hemoglobin comprises between about 8 and about 10 g/dl bovine hemoglobin solution, said hemoglobin solution comprising fractions of:
   i) at least about 95% reduced hemoglobin,
   ii) less than about 3% methemoglobin,
   iii) less than about 2% carboxyhemoglobin,
   iv) less than about 3% oxyhemoglobin, and
   v) less than about 0.3% by volume oxygen;
b) a concentration of bicarbonate ions ranges from about 17.4 to about 20.6 M; and
c) the organic buffer is HEPES buffer with a concentration range from about 20 to about 50 mM;
d) wherein the stable reference solution further comprises:
   i) a concentration of sodium selenite ranging from about 1 to about 20 µM;
   ii) a concentration of phytic acid ranging from about 0.1 to about 1.4 mM;
   iii) a concentration of reduced glutathione ranging from about 0.5 to about 8 mM;
   iv) a concentration of sodium ions ranging from about 115 to about 125 mM;
   v) a concentration of potassium ions ranging from about 2 to about 4 mM;
   vi) a concentration of calcium ions ranging from about 0.6 to about 0.8 mM;
   vii) a concentration of chloride ions ranging from about 70 to about 90 mM.

16. A stable aqueous reference solution which is contained in a sealed container having a head space consisting essentially of oxygen, wherein the $pO_2$ is less than 5 mm Hg, and a gas which is inert to the reference solution, wherein the stable aqueous reference solution comprises:
a) hemoglobin;
b) a source of bicarbonate ions; and
c) an organic buffer.

* * * * *